United States Patent
Dudley et al.

(10) Patent No.: US 9,708,075 B2
(45) Date of Patent: Jul. 18, 2017

(54) LIGHTNING PROTECTION AND DETECTION SYSTEM

(75) Inventors: Kenneth L. Dudley, Newport News, VA (US); George N. Szatkowski, Charlottesville, VA (US); Marie Woodard, Hampton, VA (US); Truong X. Nguyen, Hampton, VA (US); Jay J. Ely, Yorktown, VA (US); Chuantong Wang, Yorktown, VA (US); John J. Mielnik, North, VA (US); Sandra V. Koppen, Suffolk, VA (US); Laura J. Smith, Yorktown, VA (US)

(73) Assignee: THE UNITED STATES OF AMERICA AS REPRESENTED BY THE ADMINISTRATOR OF THE NATIONAL AERONAUTICS AND SPACE ADMINISTRATION, Washington, DC (US)

(*) Notice: Subject to any disclaimer, the term of this patent is extended or adjusted under 35 U.S.C. 154(b) by 1280 days.

(21) Appl. No.: 13/453,717

(22) Filed: Apr. 23, 2012

(65) Prior Publication Data
US 2012/0271564 A1   Oct. 25, 2012

Related U.S. Application Data

(60) Provisional application No. 61/477,845, filed on Apr. 21, 2011, provisional application No. 61/480,122, filed on Apr. 28, 2011.

(51) Int. Cl.
*G01R 31/02* (2006.01)
*B64D 45/02* (2006.01)
(Continued)

(52) U.S. Cl.
CPC ......... *B64D 45/02* (2013.01); *G01R 29/0814* (2013.01); *G01R 29/0842* (2013.01); *G01R 31/2642* (2013.01); *G01N 19/08* (2013.01)

(58) Field of Classification Search
CPC ........ H02H 3/08; H02H 9/04; G01R 19/0092; G01R 19/0084; G01R 29/0814; G01R 29/0842; G01R 31/2642; G01N 19/08
(Continued)

(56) References Cited

U.S. PATENT DOCUMENTS 4,737,705 A   4/1988   Bitar et al.
4,755,904 A * 7/1988   Brick ..................... B64D 45/02
                                                    244/1 A
(Continued)

OTHER PUBLICATIONS

EP 0549432, Machine Translation, Jun. 30, 1993.*
(Continued)

*Primary Examiner* — Huy Q Phan
*Assistant Examiner* — Raul Rios Russo
(74) *Attorney, Agent, or Firm* — Robin W. Edwards

(57) ABSTRACT

A lightning protection and detection system includes a non-conductive substrate material of an apparatus; a sensor formed of a conductive material and deposited on the non-conductive substrate material of the apparatus. The sensor includes a conductive trace formed in a continuous spiral winding starting at a first end at a center region of the sensor and ending at a second end at an outer corner region of the sensor, the first and second ends being open and unconnected. An electrical measurement system is in communication with the sensor and receives a resonant response from the sensor, to perform detection, in real-time, of lightning strike occurrences and damage therefrom to the sensor and the non-conductive substrate material.

27 Claims, 7 Drawing Sheets

(51) Int. Cl.
G01R 31/26 (2014.01)
G01R 29/08 (2006.01)
G01N 19/08 (2006.01)

(58) Field of Classification Search
USPC ......... 324/72, 72.5; 361/39, 40, 79–90, 117; 702/1, 33, 34, 85, 105, 108, 113, 127
See application file for complete search history.

(56) References Cited

U.S. PATENT DOCUMENTS

| | | | |
|---|---|---|---|
| 4,929,896 A | 5/1990 | Lara | |
| 5,291,180 A | 3/1994 | Reeb | |
| 5,361,035 A | 11/1994 | Meitzler et al. | |
| 5,541,577 A | 7/1996 | Cooper et al. | |
| 6,025,129 A | 2/2000 | Nova et al. | |
| 6,472,987 B1 | 10/2002 | Gershenfeld et al. | |
| 6,602,932 B2 | 8/2003 | Feldheim et al. | |
| 6,834,251 B1 | 12/2004 | Fletcher | |
| 6,977,504 B2 | 12/2005 | Wright et al. | |
| 7,086,593 B2 | 8/2006 | Woodard et al. | |
| 7,159,774 B2 | 1/2007 | Woodard et al. | |
| 7,683,797 B2 | 3/2010 | Woodard et al. | |
| 8,042,739 B2 | 10/2011 | Woodard et al. | |
| 8,430,327 B2 | 4/2013 | Woodard et al. | |
| 2003/0148086 A1 | 8/2003 | Pfefferle et al. | |
| 2006/0009128 A1* | 1/2006 | Hanawa | B24B 37/013 451/5 |
| 2007/0181683 A1* | 8/2007 | Woodard | H04Q 9/00 235/451 |
| 2009/0109005 A1* | 4/2009 | Woodard | G01R 33/028 340/10.4 |
| 2009/0259411 A1* | 10/2009 | Loomis | G01M 5/00 702/35 |
| 2009/0277789 A1* | 11/2009 | Woodard | G01N 29/036 204/416 |
| 2009/0302111 A1* | 12/2009 | Woodard | G08B 13/2408 235/449 |
| 2011/0102767 A1* | 5/2011 | Volanthen | G01R 29/0842 356/32 |
| 2011/0274139 A1* | 11/2011 | Woodard | G01K 7/00 374/120 |
| 2013/0192381 A1* | 8/2013 | Becker | B29C 73/10 73/802 |

OTHER PUBLICATIONS

Long, M. W. and Narciso, J. D. "Probabilistic Design Methodology for Composite Aircraft Structure", DOT/FAA/AR-99/2 Report, No. ADA365683, 1999.

Nobuo Takeda, Shu Minakuchi, Yoji Okabe, "Smart Composite Sandwich Structures for Future Aerospace Application—Damage Detection and Suppression-: a Review", Journal of Solid Mechanics and Materials Engineering vol. 1, 2007, pp. 3-17.

U. Polimeno M. Meo, "Detecting barely visible impact damage detection on aircraft composites structures", Composite Structures, vol. 91, Issue 4, Dec. 2009, pp. 398-402.

Chuantong Wang, Woodard, S.E., and Taylor, B.D.;, "Sensing of multiple unrelated tire parameters using electrically open circuit sensors having no electrical connections," IEEE Sensors Applications Symposium, New Orleans, 2009, pp. 142-147.

Robert G. Thomson and Robert J. Hayduk, "An Analysis Evaluation of The Denting Of Airplane Surfaces By Hail," NASA Technical Report No. TN D-5363, Aug. 1969.

Michael A. Fonseca, Mark G. Allen, Jason Kroh, and Jason White, "Flexible Wireless Passive Pressure Sensors for Biomedical Applications," Solid-State Sensors, Actuators, and Microsystems Workshop, Hilton Head Island, South Carolina, 2006, pp. 37-42.

Stanley E. Woodard, Qamar A. Shams, Bryant D. Taylor and Robert L. Fox, "Magnetic Field Response Measurement Acquistion System," NASA/TM-2005-213518 Langley Research Center, Hampton, Virginia, Feb. 2005.

Stanley E. Woodard and Bryant D. Taylor,"Measurement of multiple unrelated physical quantities using a single magnetic field response sensor," Measurement Science and Technology, 18 (2007), pp. 1603-1613.

Franklin A. Fisher, J. A. Plumer, and Rodney A. Perala, Lightning Protection of Aircraft, Lightning Technologies Inc., Pittsfield, MA, 1990, Chapters 3 and 4.

PCT International Search Report PCT/US07/61663, Aug. 2, 2007, pp. 1-2.

PCT International Search Report PCT/US2008/074429, Oct. 28, 2008, pp. 1-8.

PCT International Search Report PCT/US2004/013518, Jul. 21, 2005, pp. 1-9.

PCT International Search Report PCT/US2007/061675, Feb. 28, 2008, pp. 1-5.

Laura J. Smith, Kenneth L. Dudley, and George N. Szatkowski, Computational Electromagnetic Modeling of SansEC Sensors, 27th International Review of Progress in Applied Computational Electromagnetics, Williamsburg, VA, Mar. 27-31, 2011.

John J. Mielnik, Jr., "Open Circuit Resonant Sensors for Composite Damage Detection and Diagnosis," NASA/CR-2011-216884 Langley Research Center, Hampton, Virginia, Jan. 2011.

Edward Rupke, "Lightning Direct Effects Handbook", Lightning Technologies, Inc. , AGATE-WP-3.1-031027-043, Pittsfield, Mar. 1, 2002.

* cited by examiner

LIGHTNING PROTECTION AND DETECTION SYSTEM

CROSS-REFERENCE TO RELATED APPLICATIONS

This patent application claims the benefit of and priority to U.S. Provisional Patent Application Ser. Nos. 61/477,845 and 61/480,122, filed on Apr. 21, 2011 and Apr. 28, 2011, respectively, which are incorporated by reference in their entirety.

STATEMENT REGARDING FEDERALLY SPONSORED RESEARCH OR DEVELOPMENT

The present invention was made in part by employees of the United States Government and may be manufactured and used by or for the Government of the United States of America for governmental purposes without the payment of any royalties thereon or therefore.

FIELD OF THE INVENTION

The present invention relates to a protection and detection system for aircraft and aerospace vehicles. More specifically, it relates to a system for protecting against lightning and any damages therefrom.

BACKGROUND OF THE INVENTION

Aircraft and aerospace vehicles are typically formed using conductive and non-conductive materials. Some vehicles are formed of all metal material and can protect against lightning and electromagnetic interference (EMI), provide shielding effectiveness (SE) and are mechanically durable. However, there are several disadvantages to forming an aircraft using all metal material. These include weight concerns, corrosion, a coefficient of thermal expansion (CTE) mismatch, structural failure and aerodynamic design constraints. Moreover, aircraft vehicles are increasingly formed using composite materials for high strength and stiffness with minimal weight. These vehicles include composite panels for cosmetic coverings, for example, and empennage, wing, fuselage structures and turbine blades. A conventional lightning protection system for aircraft systems formed using composite materials includes embedding a metal mesh or expanded metal foil on a surface of or within laminate layers of the composite materials. As shown in FIG. 1, a conventional aircraft 100 typically includes a metal mesh surface 50 formed on a top surface of a fuselage 101, wings 102 and portions of an empennage 103 of the aircraft 100. This system has several disadvantages, such as increased weight of the aircraft 100, failure to detect lightning strikes, and failure to perform damage diagnostic due to the occurrence of a strike.

SUMMARY OF THE INVENTION

Embodiments of the present invention obviate the above-mentioned problems by providing a protection system capable of protecting an aircraft from lightning strikes, detecting lightning strike occurrences and performing diagnostic testing for damage, in real time.

According to an embodiment of the present invention, a lightning protection and detection system for an aircraft is provided. The system includes a non-conductive substrate material of the aircraft, and a sensor formed of a conductive material and deposited on the non-conductive substrate material of the aircraft. The sensor includes a conductive trace formed in a continuous spiral winding starting at a first end at a center, region of the sensor and ending at a second end at an outer corner region of the sensor, the first and second ends being open and unconnected. The system further includes an electrical measurement system in communication with the sensor and configured to receive a resonant response from the sensor, to perform detection, in real-time, of lightning strike occurrences and damage therefrom to the sensor and the non-conductive substrate material.

According to another embodiment of the present invention, the system includes a non-conductive substrate material of the aircraft, and a sensor array comprising a plurality of sensors coupled together in series with each sensor formed of a conductive material and the sensor array being deposited on the non-conductive substrate material of the aircraft. Each sensor includes a conductive trace formed in a continuous spiral winding starting at a first end at a center region of the sensor and ending at a second end at an outer corner region of the sensor, the first and second ends being open and unconnected. The system further includes an electrical measurement system in communication with the sensor and configured to receive a resonant response from the sensor, to perform detection, in real-time, of lightning strike occurrences and damage therefrom to the sensor and the non-conductive substrate material.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION OF THE INVENTION

Embodiments of the present invention provide a lightning protection and detection system for protecting aircraft (e.g., commercial aircrafts) and aerospace vehicles (e.g., satellites, wind turbines) against direct and indirect effects of lightning strikes. Specifically, the system provides lightning strike mitigation to airframe and aircraft systems, real-time detection and sensing of lightning strikes to the airframe, and in-flight diagnostic testing of damage to the fuselage and other airframe structures of the aircraft. The protection sensor system of the present invention may be adaptable to other industries and applications. Thus, the present invention is not limited to being used within aircraft and aerospace vehicles and may be applied to any type of vehicle or other apparatus being formed of composite materials, such as wind turbines, automobiles and ships. The composite materials may include polymers, metals, and ceramics, for example, which act as a matrix and hold reinforcement material to a desired shape. Composite materials formed from fiberglass and carbon (i.e., graphite), are widely used and have a high strength-to-weight ratio compared to metallic structures. The composite materials may include several layers or plies of the reinforcement material. Delamination of the layers may occur due to lightning strike occurrences. The present invention is able to detect and protect against lightning strike occurrences.

Figure 1:
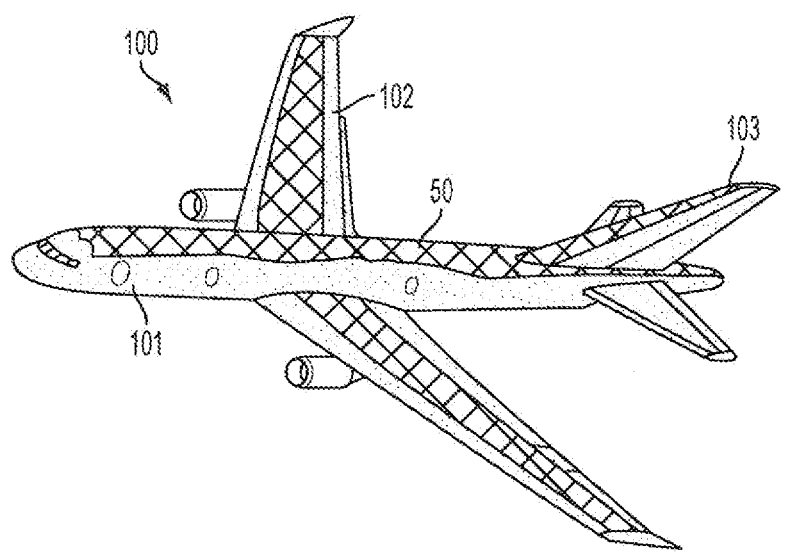
FIG. 1 illustrates a conventional protection system of an aircraft.

A sensor 220 of the lightning protection and detection system will now be discussed with reference to FIGS. 2A and 2B. According to an embodiment of the present invention, the sensor 220 is an open circuit resonant sensor capable of detecting damage to composite materials of the aircraft (e.g., aircraft 100 shown in FIG. 1). The sensor 220 is a passive open circuit which does not require any direct electrical connections to a generating source. Although passive, the sensor 220 is energized by an electromagnetic field generated remotely from the sensor 220 and produces magnetic field responses when electrically stimulated.

According to an embodiment, the sensor 220 is formed of a conductive material. Further, the sensor 220 is an inductor in the form of a planar spiral as shown in FIG. 2A. The sensor 220 uses inherent capacitance and resistance of a geometric shape thereof (e.g., the square shape as depicted in FIG. 2) to generate a resonant response (e.g., frequency, amplitude, bandwidth, phase and harmonics). Even if damaged, the sensor 220 still functions but with a different resonant response. That is, a frequency thereof, for example, may be different compared to that of an undamaged sensor 220.

Figure 2A:
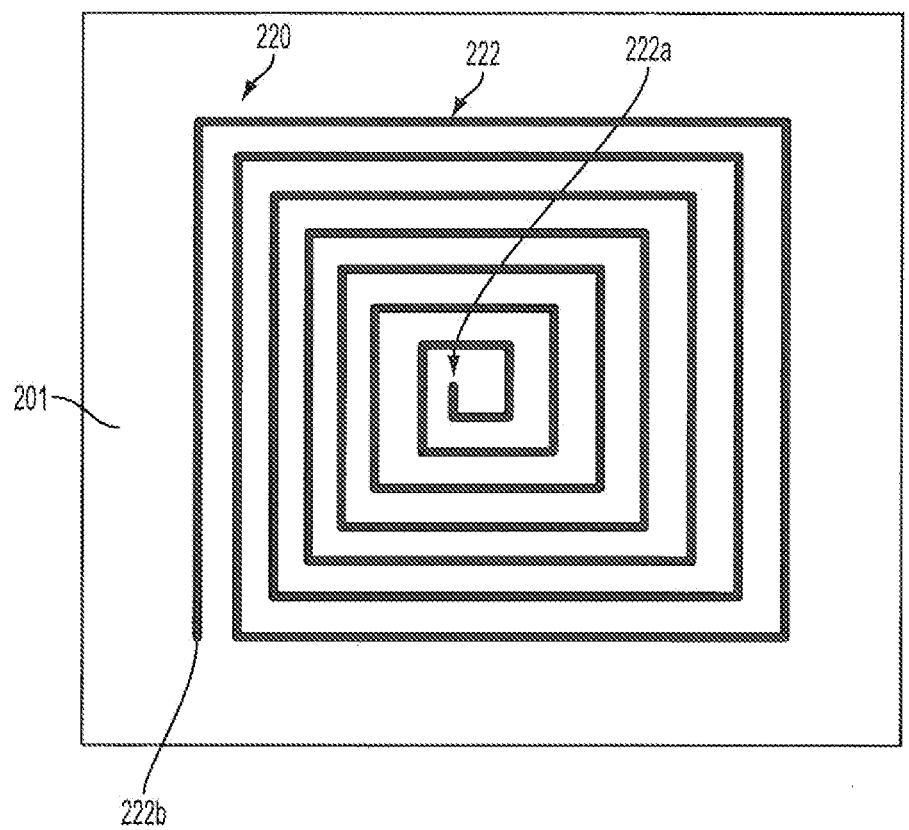
FIG. 2A is a schematic view of a sensor of a lightning protection and detection system that can be implemented within embodiments of the present invention.
Figure 2B:
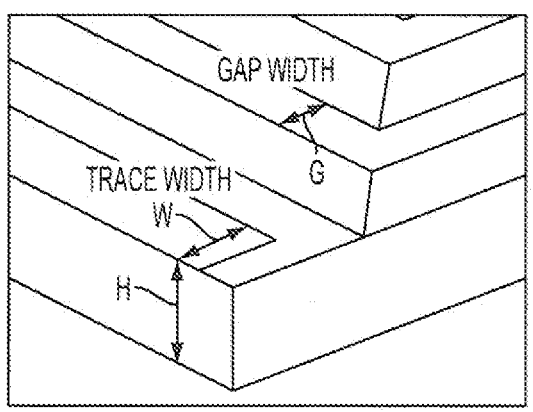
FIG. 2B is an exploded view of a portion of the sensor shown in FIG. 2A.
Figure 4C:
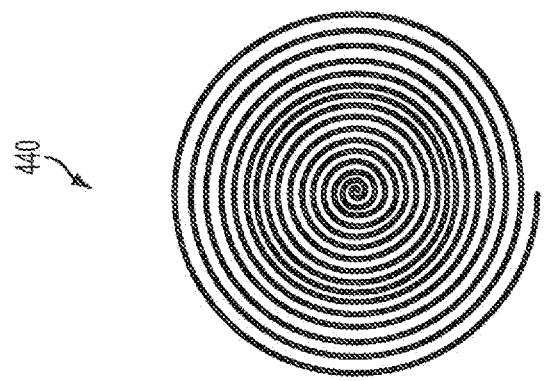
FIGS. 4A through 4C are schematic view of sensors of the lightning protection and detection system that can be implemented within alternative embodiments of the present invention.
Figure 4B:
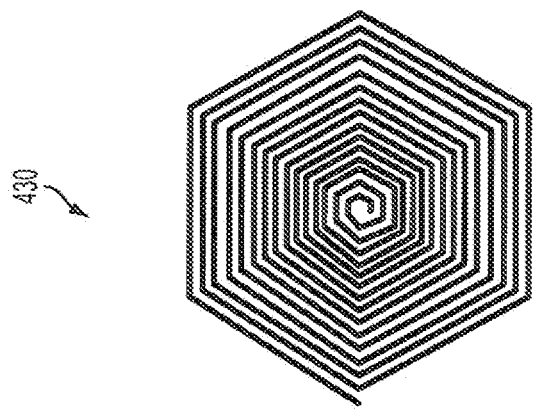
Figure 4A:
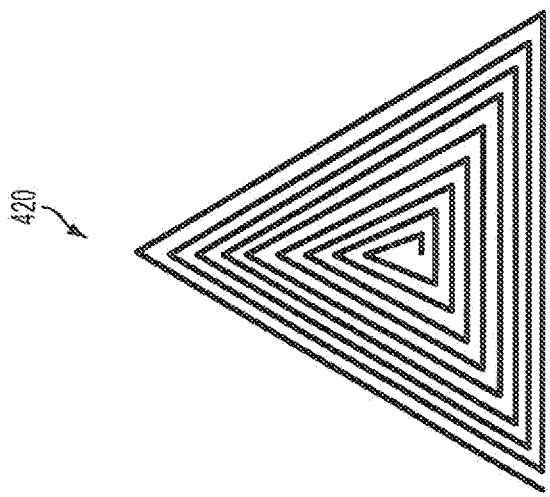

According to one embodiment, the sensor 220 is formed in a geometric pattern such as a square as shown in FIG. 2A. The sensor 220 may be formed having outer dimensions ranging from 2 inches (e.g., in a 2 inch×2 inch configuration) to 9 inches (e.g., 9 inch×9 inch configuration). The present invention is not limited to the sensor 220 being of a particular shape or size. Thus, the sensor 220 may vary in size and be formed in a triangular, hexagonal and circular shape (as depicted in FIGS. 4A through 4C), for example.

The sensor 220 is formed of metal foil (e.g., copper) having a predetermined thickness of approximately 1.25 mils, and includes a conductive trace 222 formed from the metal foil which is a continuous spiral winding starting at a first end 220a at a center region of the sensor 220 and ending at a second end 220b at an outer corner region of the sensor 220, with the first and second ends open and unconnected. According to embodiments of the present invention, the trace 222 is not limited to being formed of a particular conductive material and may vary accordingly. For example, the trace 222 may be formed of aluminum, brass, copper, monel, mu-metal, nickel, palladium, platinum, silver, steel, stainless steel, titanium, zinc, and structural composite derivatives such as fibers, cloths, and tapes plasma sprayed or vapor deposited with the above-mentioned metals.

The trace 222 is a thin film conductive material and is approximately 93.75 mils wide W having a gap G of approximately 31.25 mils therebetween, when in a spiral configuration. The present invention is not limited to the trace width W and gap G being of a particular size. According to an embodiment, trace widths W and gaps G can vary according to the design of the sensor 220 and sensor array 500 (shown in FIG. 5). For example, trace widths W may range from approximately 50 mils to 1000 mils and trace gaps G may range from approximately 30 mils to 350 mils.

According to an embodiment of the present invention, some techniques for forming the sensor 220 include conventional metal conductor deposition processes including thin film fabrication techniques. The present invention is not limited to forming the sensors 220 via a particular technique, and any suitable technique may be utilized. Some other techniques include die cut or stamped thin metal foils, appliqués, conductive paint or silk screening techniques, and structural composite techniques such as metal conductor plasma sprayed or vapor deposited on to, fibers, cloths, and tapes in the form of the sensor 220 and sensor array 500.

According to an embodiment, the sensor resonant response is dependent upon the geometric pattern of the sensor 220 and the impedance of the coupled material (i.e., the substrate 201). In one embodiment, the resonant response (e.g., resonant frequency) of the sensor 220 increases as the size of the sensor 220 decreases. The sensor 220 is configured to detect an abrupt change in a resonant response thereof, to support damage diagnosis. Additional details regarding the detection process will be discussed below with reference to FIG. 8.

Additional details of the sensor 222 will now be discussed with reference to FIG. 2B. As shown in FIG. 2B, the trace width W, the trace gap G, between the conductive legs of the spiral trace 222, and the substrate 201 thickness H may vary, based upon desired design characteristics. The length of the trace 222 of the sensor 220 is further parameterized by the area of the trace 222. This area determines the sensor size which directly relates to the design operation frequency and the amount of composite material surface 201 that the sensor 222 covers. Also, according to an embodiment of the present invention, a number of turns within the trace 222 that comprise inductive loops of the sensor 220 is also parameterized.

An inductance of the sensor 220 is equal to a sum of self and mutual inductances of trace interactions. The self-inductance is a measure of the magnetic field generated by a time-varying current. Mutual inductance is the measure of mutually coupled magnetic fields of adjacent traces with current flowing in a same direction. A capacitance of the sensor 220 is determined based on the trace width W between the spiral trace 222 and a substrate 201 (e.g., the composite surface of the aircraft) which acts as a dielectric. The capacitance is considered to be parasitic and is minimal in a geometric spiral with the non-conductive substrate 201.

According to an embodiment, the resistance of the sensor 220 is determined based on overall trace dimensions (i.e., width W and gap width G and length L of the trace 222). The total resistance of a planar spiral is a combination of series and parallel resistance. Series resistance is both dependent and independent on the frequency. The independent portion is, essentially the direct current (D.C.) resistance of the wire (i.e., the trace 222), and is largely dependent on the total length L. The frequency dependent portion of the overall resistance is due to the effects of eddy currents. The parallel resistance is a result of the finite resistance between the substrate material 201 and the sensor 220.

The electric field generated due to a magnetic flux of the trace 222 is confined within the substrate 201. At higher frequencies, the electric field becomes large enough that it capacitively couples through the substrate 201. This is the self-resonance frequency (SRF) of the sensor 220 combined with the substrate 201. The effect associated with the trace 222 induces currents of the substrate 201. The currents of the substrate 201 are mainly composed of two parts: displacement currents from the trace 222 to the substrate 201 through capacitance, and eddy currents in the substrate 201. The displacement currents are a product of the time varying electric field through capacitance, and increase with higher frequencies. The eddy currents are a product of the sensor 220 time-varying magnetic field penetrating the substrate 201. The induced currents in the substrate 201 flow in opposite direction to the current flow of the sensor 220, producing a counter effect on the performance of the sensor 220 and substrate 201 when attached together. The detection of the differences in frequency and amplitude of the induced currents within the substrate 201 provides a means of detecting damage or changes to the state and condition of the substrate 201. Additional details regarding the sensor 220 are disclosed in co-pending U.S. Patent Publication 2007/0181683 (application Ser. No. 11/671,089) filed Feb. 5, 2007, entitled "WIRELESS SENSING SYSTEM USING OPEN-CIRCUIT ELECTRICALLY-CONDUCTIVE SPIRAL-TRACE SENSOR" by Woodard et al., and U.S. Pat. No. 8,042,739 (application Ser. No. 11/864,012 filed Sep. 28, 2007); entitled "WIRELESS TAMPER DETECTION SENSOR AND SENSING SYSTEM" by Woodard et al. The contents of both are hereby incorporated by reference in their entirety and may be repeated herein to provide a complete description of the present invention.

Figure 3:
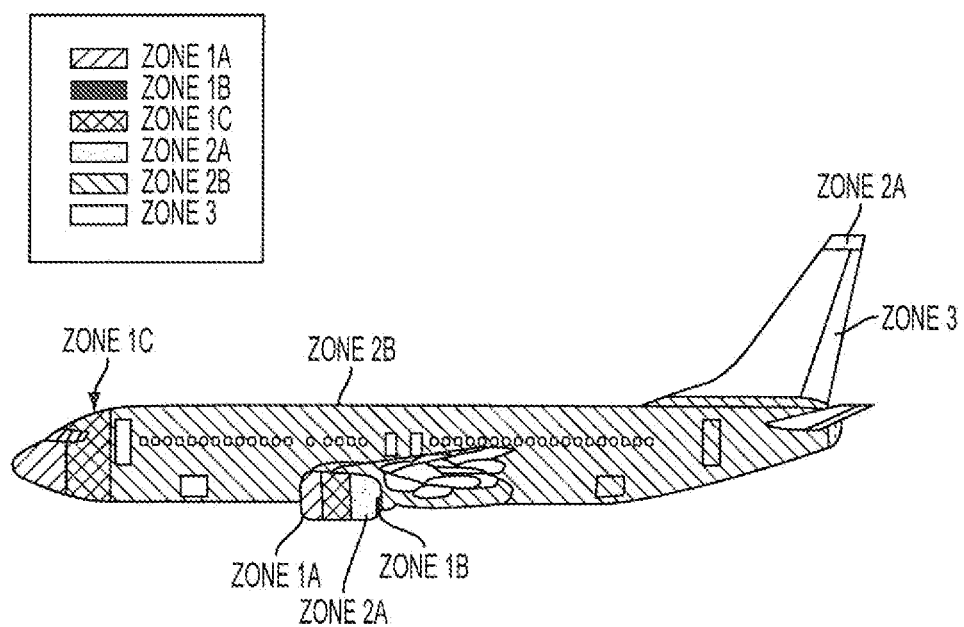
FIG. 3 is a schematic view of lightning zones of an aircraft that can be implemented within embodiments of the present invention.

The sensor 220 may be formed as a single appliqué on a substrate 201 (i.e., a composite panel of the aircraft) or at multiple locations on the aircraft. FIG. 3 is a schematic view of lightning zones of an aircraft that can be implemented within embodiments of the present invention.

Figure 5:
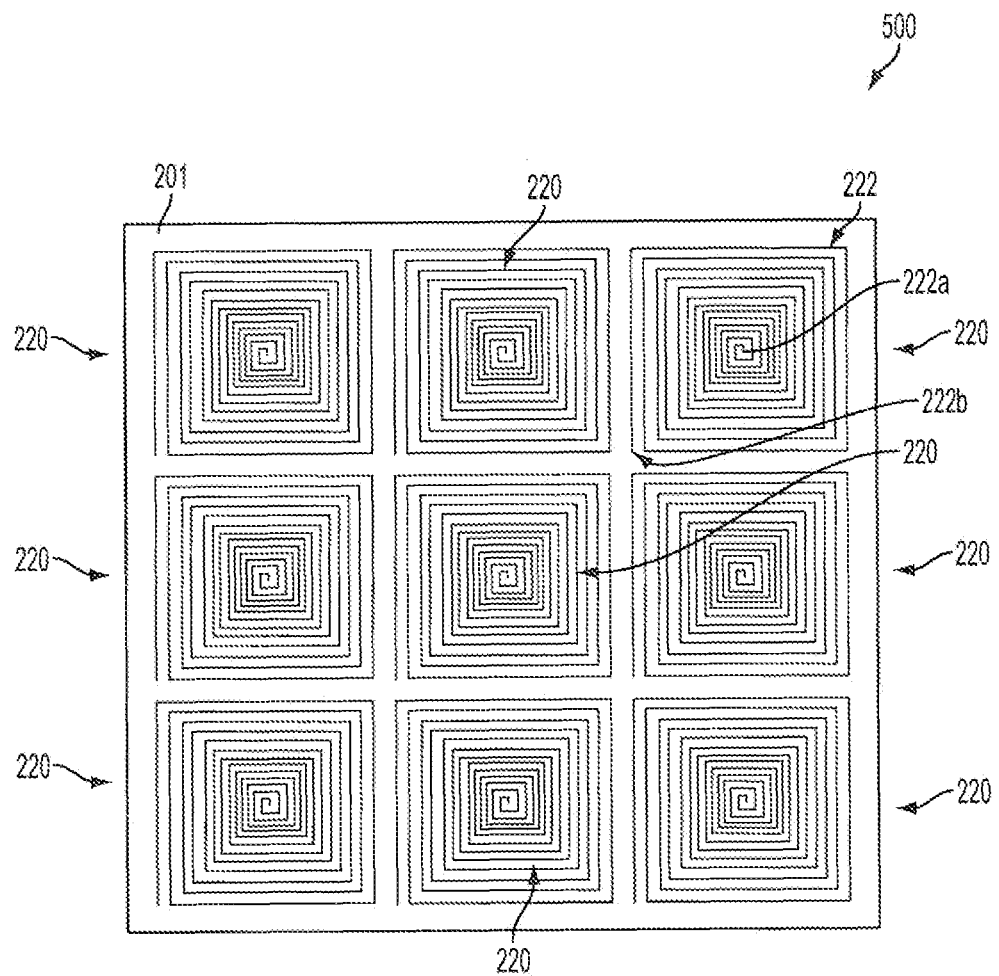
FIG. 5 is a schematic view of a sensor array including a plurality of sensors that can be implemented within embodiments of the present invention.

The sensors 220 and/or sensor arrays 500 (as depicted in FIG. 5) are located in zone locations defined based on the aircraft type where lightning leaders are likely to be attached. These locations are known as "Lightning Zones" and are defined by initial lightning attachment points, lightning swept strokes, and conducted current channels. As shown in FIG. 3, the lightning zones include, for example, Zone 1A, Zone 1B, Zone 1C, Zone 2A, Zone 2B, and Zone 3. According to an embodiment, these zones are determined by high voltage tests on scale models and lightning strike service history on aircrafts of a similar type. A number and configuration of the sensors 220 and sensor arrays 500 is dependent upon the zone definitions of the aircraft to be protected. According to one embodiment, the sensor 220 is attached directly to the substrate 201 by an adhesive material. In one embodiment, the metal foil of the sensor 220 may be formed with an adhesive backing thereon. In another embodiment, various adhesives may be used to attach the sensor 220 to the substrate 201. Suitable adhesives include epoxies, such as but not limited to, 3M™ Scotch-Weld™ structural adhesives including structural adhesive EC 3710 and lightning strike protection adhesive film AF 163-2. The adhesives should have a high bond strength and/or high peel strength at low and elevated temperatures approximately −60 F to 250 F. Suitable applications include spray, paint on or adhesive film.

The sensor 220 is capable of permeating through the substrate 201 (i.e., composite materials) of the specific zones, for damage diagnosis. Further, the sensor 220 is capable of performing partial electromagnetic penetration to discern between top layer damage and delamination between inner plies of the substrate 201.

According to an embodiment of the present invention, the sensor of the protection and detection system may be formed of varying shapes as shown in FIGS. 4A through 4C. For example, in FIG. 4A, a sensor 420 is formed in the shape of a triangle. In. FIG. 4B, a sensor 430 is formed in the shape of a hexagon. In FIG. 4C, a sensor 440 is formed in the shape of a circle. The determination of the capacitance and inductance of the sensors 420, 430 and 440 is based on the corresponding shape thereof.

FIG. 5 is a schematic view of a sensor array of a protection system that can be implemented within embodiments of the present invention. As shown in FIG. 5, the sensor array 500 includes a plurality of sensors 220. The sensor array 500 may include a predetermined number of sensors 220 in a range of between two (2) to nine (9) sensors 220, for example. The sensor array 500 may include sensors 420, 430 or 440 or a combination thereof. According to an embodiment of the present invention, the present invention is not limited to the sensor being of a particular geometric shape. There area variety of spiral sensor 220 and array 500 geometric shapes that may be tailored to specific aircraft lightning protection and sensory needs. Further, an array 500 of sensors may consist of any variety of individual sensor geometries to tile or cover the lightning zone or zones (e.g., Zone 1A, Zone 1B, Zone 1C, Zone 2A, Zone 2B, Zone 3) of a particular aircraft. A specific tiling pattern of the array 500 is determined to mitigate lightning attachment points and/or redirects lightning strike continuous currents to a less critical structure or protected hard points of the aircraft. Additional details regarding the sensor array 500 are disclosed in U.S. Pat. No. 7,683,797 (application Ser. No. 11/671,131 filed on Feb. 5, 2007), entitled "DAMAGE DETECTION/LOCATING SYSTEM PROVIDING THERMAL PROTECTION" by Woodard et al., the contents of which are hereby incorporated by reference in their entirety and may be repeated herein to provide a complete description of the present invention.

In the event of a lightning strike occurrence, lightning currents are concentrated at the outer corner 222b of one of the sensors, for example, the current propagates to the conductive pathway and not across the sensor, array 500. The electrical impedance and intrinsic ability of each sensor 220 allows it to steer lightning currents, to thereby perform lightning mitigation. Even when damaged, a single sensor 220 or multiple coupled sensors 220 within the sensor array 500 maintains functionality thereof.

Figure 6:
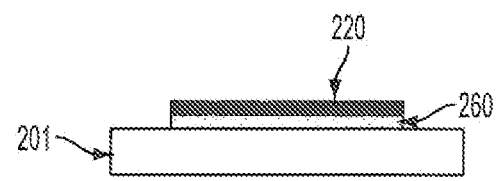
FIG. 6 is a schematic view of a lightning protection and detection system that can be implemented within alternative embodiments of the present invention.

According to another embodiment, the sensors 220 may also be applied to semi-conductive or more conductive composite structures and materials of aircrafts. FIG. 6 is a schematic view of a lightning protection and detection system that can be implemented within alternative embodiments of the present invention. As shown in FIG. 6, the lightning protection and detection system includes a conductive layer 260 formed between the substrate 201 and the sensor 220. The layer 260 controls a coupling between the sensor 220 and the substrate 201. According to one embodiment, layer 260 is formed of any material having a high level of permeability and/or conductivity. The layer 260 is not limited to being formed in any particular design, and may vary as needed. FIGS. 7A through 7D are schematic views of a high permeable conductive material layer of the lightning protection and detection system of FIG. 6 that can be implemented within alternative embodiments of the present invention.

Figure 7A:
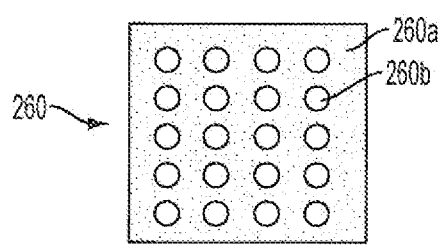
FIGS. 7A through 7D are schematic top views of a high permeable conductive material layer of the lightning protection and detection system of FIG. 6 that can be implemented within alternative embodiments of the present invention.
Figure 7B:
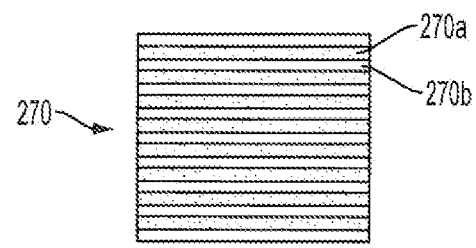
Figure 7C:
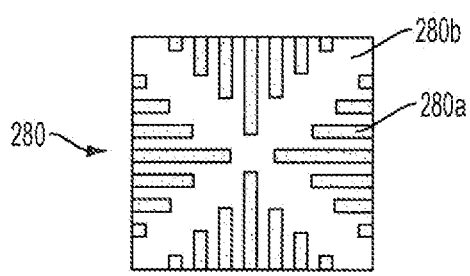
Figure 7D:
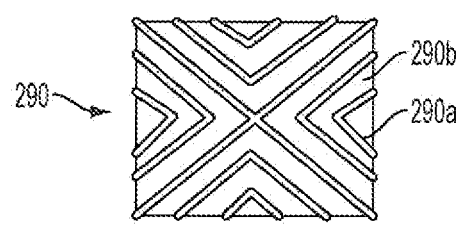

As shown in FIG. 7A, layer 260 includes a plurality of holes forming a covered region 260a, and non-covered, regions 260b corresponding to the substrate 201. As shown in FIG. 7B, a conductive layer 270 is formed similar to layer 260, and includes covered regions 270a and non-covered regions 270b alternately arranged in a line pattern. Further, in FIG. 7C, a conductive layer 280 is formed having covered regions 280a formed having a plurality of line regions grouped together and facing each other from opposite ends of the layer 280 and a non-covered region 280b therebetween. In yet another embodiment, a conductive layer 290 is provided and is formed of covered regions 290a including a plurality of lines arranged in angled positions, and non-covered regions 290b formed therebetween. The present invention is not limited to using only the patterns of conductive layers 260, 270, 280 or 290 between the sensor 220 and the substrate 201. According to other embodiments, any patterns providing coverage larger than 0% and up to 100% may be used to control coupling between the sensor 220 and the substrate 201.

Real-time detection and sensing of lightning strikes to the airframe, and in-flight diagnostic testing of damage of the protection and detection system is performed via an electrical measurement system in communication with the sensors 220 which will now be described below with reference to FIG. 8.

Figure 8:
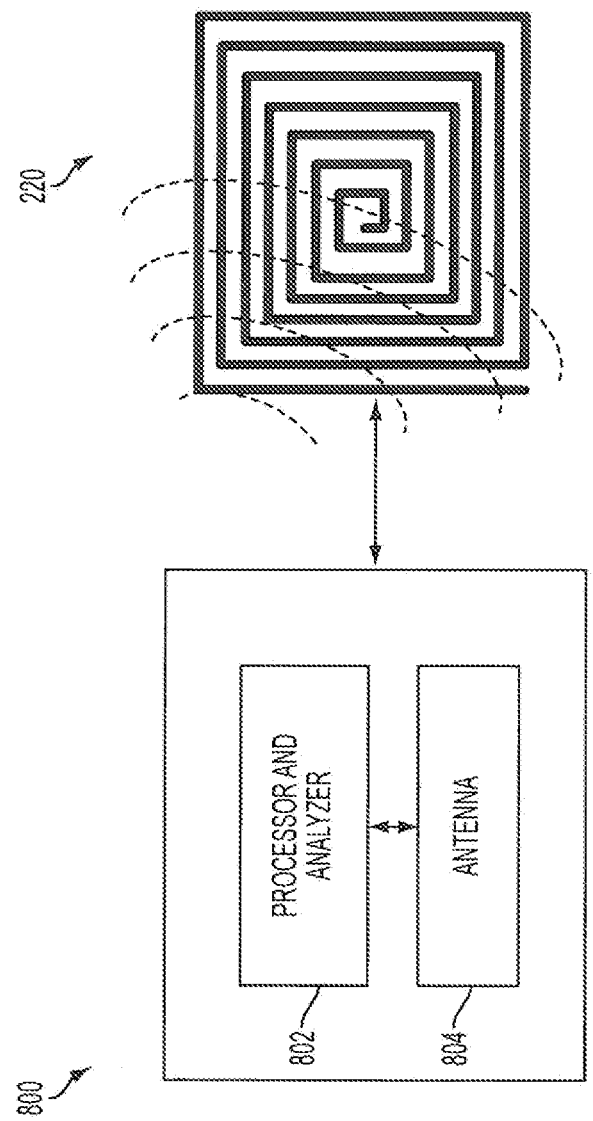
FIG. 8 is a diagram illustrating an electrical measurement system in communication with the sensors that can be implemented within embodiments of the present invention.

FIG. 8 is a diagram illustrating an electrical measurement system 800 for measuring the resonant response of the sensor 220. The electrical measurement system 800 includes a processor/analyzer 802 and an antenna 804 in communication with the sensor 220. The system 800 is able to measure frequency, amplitude, bandwidth, phase and harmonics related to the sensor 220. The processor/analyzer 802 may be a network analyzer, for example. The antenna 804 may be a square loop antenna or any directive antenna. A height of the antenna 804 above the sensor 220 is adjustable. The antenna 804 may be positioned in a near field or a far field and is used to electromagnetically excite the sensor 220 or sensor array 500 and read back the resonant response thereof. The electric field generated due to a planar resonant spiral inductor's magnetic flux is coupled to and confined within the substrate of the dielectric material. At higher frequencies, the electric field becomes large enough that it capacitively couples through the material substrate. This is the self-resonance frequency (SRF) of the sensor 220 combined with the substrate 201. This effect associated with the sensor 220 induces currents in the substrate 201. The substrate currents are mainly composed of two parts: displacement currents from spiral traces 222 to the substrate 201 through capacitance, and eddy currents in the substrate 201. The displacement currents are a product of the time varying electric field through capacitance, and increase with higher frequencies. The eddy currents are a product of the sensor 220 time-varying magnetic field penetrating the substrate 201. The induced currents in the substrate 201 flow in an opposite direction to the current flow of the sensor 220, producing a counter effect on the performance of the sensor 220 in combination with the substrate 201. The detection of the differences in frequency and amplitude of the induced currents within the substrate 201 (due to a defect in the material such as a hole, or void, or crack, or delamination) offers a means of detecting damage or changes to the state and condition of the substrate 201.

According to other embodiments, the electrical measurement system 800 may function as a magnetic field recorder as disclosed in U.S. Pat. No. 7,086,593 (application Ser. No. 10/839,445 filed Apr. 30, 2004), entitled "MAGNETIC FIELD RESPONSE MEASUREMENT ACQUISITION SYSTEM" by Woodard et al. and U.S. Pat. No. 7,159,774 (application Ser. No. 11/305,854 filed. Dec. 16, 2005), entitled "MAGNETIC FIELD RESPONSE MEASUREMENT ACQUISITION SYSTEM" by Woodard et al. The contents of both are hereby incorporated by reference in their entirety and may be repeated herein to provide a complete description of the present invention. The processor/analyzer 802 includes algorithms embodied within software for controlling antenna 804 and analyzing RF signals received from the sensor(s) 220. The processor/analyzer 802 modulates an input signal that is, then supplied to antenna 804 so that the antenna 804 produces either a broadband time-varying magnetic field or a single harmonic field. The antenna 804 receives harmonic magnetic responses produced by the sensor(s) 220. The antenna 804 may be two separate antennas or a single antenna as shown which handles both transmission and receiving operations (as indicated by the arrow shown in FIG. 8). In order to perform real-time damage detection, the sensors 220 are interrogated by the electrical measurement system 800. The interrogation is performed by establishing a baseline or calibration response when the sensors are in an undamaged state while adhered to the composite panel or structure of the aircraft. With the baseline response established, the sensors 220 can be interrogated by the electrical measurement system 800 on a continual (i.e., in real-time), periodic, or on-demand basis to see if any damage has occurred due to lightning strikes.

Embodiments of the present invention provide a multi-functional protection and detection system that protects against lightning, detects any damages therefrom and provides shielding against electromagnetic effects. The system protects the aircraft against the effects of lightning, minimizes the effects, and directs resulting electrical current so as not to endanger the aircraft or aerospace vehicle.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated While the preferred embodiment to the invention has been described, it will be understood that those skilled in the art, both now and in the future, may make various improvements and enhancements which fall within the scope of the claims which follow. These claims should be construed to maintain the proper protection for the invention first described.

What is claimed as new and desired to be secured by Letters Patent of the United States is:

1. A lightning protection and detection system for an apparatus, comprising:
    a substrate material of the apparatus;
    a sensor formed of a conductive material and deposited on the substrate material of the apparatus, the sensor including a conductive trace formed in a continuous spiral winding starting at a first end at a center region of the sensor and ending at a second end at an outer corner region of the sensor, the first and second ends being open and unconnected; and
    an electrical measurement system in communication with the sensor and configured to receive a resonant response from the sensor,
    wherein the sensor is configured to propagate a lightning current resulting from a lightning strike occurrence along the conductive trace, and
    wherein the electrical measurement system is configured to detect, in real-time, a change in the resonant response, said change in resonant response indicative of the lightning strike occurrence and damage therefrom to the sensor and the substrate material.

2. The lightning protection and detection system of claim 1, wherein the apparatus is an aircraft or an aerospace vehicle.

3. The lightning protection and detection system of claim 1, wherein the substrate material is non-conductive and the conductive trace is formed of a thin film conductive material.

4. The lightning protection and detection system of claim 3, wherein the thin film conductive material is copper.

5. The lightning protection and detection system of claim 1, wherein the sensor is energized by an electromagnetic field generated remotely from the sensor and is configured to generate the resonant response when electrically stimulated.

6. The lightning protection and detection system of claim 1, wherein the resonant response includes at least one of frequency, amplitude, bandwidth, phase and harmonics corresponding to the sensor.

7. The lightning protection and detection system of claim 1, wherein the electrical measurement system comprises:
    an antenna configured to transmit to and receive signals from the sensor, including the resonant response; and
    a processor and analyzer in communication with the antenna and configured to detect and analyze the signals received from the sensor to detect lightning strike occurrences and damage due to the lightning strike occurrence.

8. The lightning protection and detection system of claim 5, wherein the electrical measurement system is configured to establish a baseline resonant response for the sensor while undamaged wherein changes from the baseline resonant response indicate damage to the sensor.

9. The lightning protection and. detection system of claim 1, wherein the sensor is formed in a shape of at least one of a square, triangle, hexagon or circle.

10. The lightning protection and detect on system of claim 9, wherein the resonant response varies based on the Shape of the sensor.

11. The lightning protection and detection system of claim 9, wherein a resistance and capacitance of the sensor is based on the shape of the conductive trace, wherein the resistance is determined based on overall dimensions of the conductive trace and the capacitance is determined based on a width between the conductive trace and the substrate material.

12. The lightning protection and detection system of claim 1 wherein the substrate material is conductive, further comprising:
    a high permeable or conductive layer formed between the substrate material and the sensor and configured to control a coupling between the sensor and the substrate material,
    wherein the high permeable or conductive layer is formed of at least one covered region and at least one non-covered region, to cover greater than 0% and up to 100% of the substrate material.

13. The lightning protection and detection system of claim 2, wherein the sensor is located in a predetermined lightning zone location of the aircraft or the aerospace vehicle.

14. A lightning protection and detection system for an apparatus, comprising:
    a substrate material of the apparatus;
    a sensor array comprising a plurality of sensors coupled together in series, each sensor formed of a conductive material and the sensor array being deposited on the substrate material, each sensor including a conductive trace funned in a continuous spiral winding starting at a first end at a center region of the sensor and ending at a second end at an outer corner region of the sensor, the first and second ends being open and unconnected; and
    an electrical measurement system in communication with the sensors and configured to receive a resonant response from the sensors,
    wherein each of the plurality of sensors is configured to propagate a lightning current resulting from a lightning strike occurrence along an associated conductive trace, and
    wherein the electrical measurement system is configured to detect, in real time, a change in the resonant response, said change in resonant response indicative of the lightning strike occurrence and damage therefrom to the sensor and the substrate material.

15. The lightning protection and detection system of claim 14, wherein the apparatus is an aircraft or an aerospace vehicle.

16. The lightning protection and detection system of claim 14, wherein the substrate material is non--conductive and the conductive trace is formed of a thin film conductive material.

17. The lightning protection and detection system of claim 16, wherein the thin film conductive material is copper.

18. The lightning protection and detection system of claim 14, wherein each sensor is energized by an electromagnetic field generated remotely from the sensor and is configured to generate the resonant response, when electrically stimulated.

19. The lightning protection and detection system of claim 14, wherein the resonant response includes at least one of frequency, amplitude, bandwidth, phase and harmonics corresponding to the sensor.

20. The lightning protection and detection system of claim 14, wherein the electrical measurement system comprises:
   an antenna configured to transmit to and receive signals from the sel sors, including the resonant response; and
   a processor and analyzer in communication with the antenna and configured to detect and analyze the signals received from the sensors to detect lightning strike occurrences and damage due to the lightning strike occurrence.

21. The lightning protection and detection system of claim 14, wherein the electrical measurement system is configured to establish a baseline resonant response for the sensor while undamaged wherein changes from the baseline resonant response indicate damage to the sensors.

22. The lightning protection and detection system of claim 14, wherein the sensor is formed in a shape of at least one of a square, triangle, hexagon or circle.

23. The lightning protection and detection system of claim 22, wherein the resonant response varies based on the shape of the sensors.

24. The lightning protection and detection system of claim 22, wherein a resistance and capacitance of the sensors is based on the shape of the conductive trace, wherein the resistance is determined based on overall dimensions of the conductive trace and the capacitance is determined based on a width between the conductive trace and the substrate material.

25. The lightning protection and detection system of claim 22, wherein an inductance of the sensors is equal to a sum of self and mutual inductances of trace interactions of the conductive traces of the sensors within the sensor array.

26. The lightning protection and detection system of claim 14, wherein the substrate material is conductive, further comprising:
   a high permeable or conductive layer formed between the substrate material and the sensors of the sensor array and configured to control a coupling between the sensors and substrate material,
   wherein the high permeable or conductive layer is formed of at least one covered region and at least one non-covered region, to cover greater than 0% and up to 100% of the substrate material.

27. The lightning protection and detection system of claim 15, wherein the sensor array is located in a predetermined lightning zone location of the aircraft or the aerospace vehicle.

* * * * *

UNITED STATES PATENT AND TRADEMARK OFFICE
CERTIFICATE OF CORRECTION

PATENT NO. : 9,708,075 B2
APPLICATION NO. : 13/453717
DATED : July 18, 2017
INVENTOR(S) : Kenneth L. Dudley et al.

It is certified that error appears in the above-identified patent and that said Letters Patent is hereby corrected as shown below:

On the Title Page

Item (75), at Column 1, Lines 3 and 4:
Replace "Marie Woodard" with --Stanley E. Woodard--

Signed and Sealed this
Twelfth Day of June, 2018

Andrei Iancu
*Director of the United States Patent and Trademark Office*